United States Patent
Dede et al.

(10) Patent No.: US 12,053,558 B2
(45) Date of Patent: Aug. 6, 2024

(54) VEHICLE SANITIZER SYSTEM AND METHOD OF SANITIZING A VEHICLE

(71) Applicant: Toyota Motor Engineering and Manufacturing North America, Inc., Plano, TX (US)

(72) Inventors: Ercan M. Dede, Ann Arbor, MI (US); Paul D. Schmalenberg, Pittsburgh, PA (US); Atsushi Iwai, Pittsburgh, PA (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 678 days.

(21) Appl. No.: 17/221,938

(22) Filed: Apr. 5, 2021

(65) Prior Publication Data

US 2022/0313856 A1    Oct. 6, 2022

(51) Int. Cl.
*A61L 2/24*    (2006.01)
*A61L 2/14*    (2006.01)
(Continued)

(52) U.S. Cl.
CPC ...... *A61L 2/24* (2013.01); *A61L 2/14* (2013.01); *B60H 3/0078* (2013.01); *B60N 2/002* (2013.01);
(Continued)

(58) Field of Classification Search
CPC .......... A61L 2/24; A61L 2/14; A61L 2202/11; A61L 2202/14; A61L 2202/25;
(Continued)

(56) References Cited

U.S. PATENT DOCUMENTS

| | | | | |
|---|---|---|---|---|
| 5,656,063 A | * | 8/1997 | Hsu | B03C 3/017 |
| | | | | 422/4 |
| 9,782,504 B2 | * | 10/2017 | Holub | H05B 47/115 |

(Continued)

FOREIGN PATENT DOCUMENTS

| | | |
|---|---|---|
| CN | 103373213 A | 10/2013 |
| CN | 103287242 B | 5/2015 |

(Continued)

OTHER PUBLICATIONS

"Plasma for automobile manufacturing," www.plasmatreat.com/industrial-applications/plasmatreatment_automotive-industry.html, retrieved on Mar. 31, 2021, 7 pages.

*Primary Examiner* — Gertrude Arthur Jeanglaude
(74) *Attorney, Agent, or Firm* — Jordan IP Law, LLC (57) ABSTRACT

A vehicle sanitizer system includes a sanitizer emitter member, selectively moveable between a stowed position in a compartment of a vehicle cabin and a deployed position out of the compartment; a sensor module to detect an interior of a vehicle cabin as sensor data; and a vehicle sanitizer module, that includes one or more processors to execute a set of instructions that cause the vehicle sanitizer module to: conduct, in response to the detection, an analysis of the sensor data; identify, in response to the analysis, one or more target interior surfaces in the vehicle cabin to be sanitized; and cause, via the sanitizer emitter member and in response to the identification, generation of water vapor content into the vehicle cabin, one or more sanitizer streams directed at the identified one or more target interior surfaces.

20 Claims, 5 Drawing Sheets

(51) Int. Cl.
    *B60H 3/00*         (2006.01)
    *B60N 2/00*         (2006.01)
    *B60S 1/64*         (2006.01)
    *G06V 20/59*       (2022.01)
    *H05H 1/24*        (2006.01)

(52) U.S. Cl.
    CPC ............... *B60S 1/64* (2013.01); *G06V 20/59* (2022.01); *H05H 1/24* (2013.01); *A61L 2202/11* (2013.01); *A61L 2202/14* (2013.01); *A61L 2202/25* (2013.01)

(58) Field of Classification Search
    CPC ...... G06V 20/59; B60H 3/0078; B60N 2/002; B60S 1/64; H05H 1/24
    See application file for complete search history.

(56) References Cited

U.S. PATENT DOCUMENTS

| | | | |
|---|---|---|---|
| 10,646,605 | B2 | 5/2020 | Roy et al. |
| 10,752,358 | B2 * | 8/2020 | Hills ................. D06F 58/10 |
| 11,584,196 | B2 * | 2/2023 | Kyle ................. B60H 3/0658 |
| 2018/0050122 | A1 * | 2/2018 | Lin ...................... A61L 2/24 |
| 2019/0091738 | A1 * | 3/2019 | Chen ................ B60H 1/00742 |
| 2022/0023478 | A1 * | 1/2022 | Childress ................ A61L 2/28 |

FOREIGN PATENT DOCUMENTS

| | | |
|---|---|---|
| CN | 108980771 A | 12/2018 |
| CN | 107029271 B | 2/2020 |
| KR | 20180091530 A | 8/2018 |

\* cited by examiner

VEHICLE SANITIZER SYSTEM AND METHOD OF SANITIZING A VEHICLE

TECHNICAL FIELD

Embodiments relate generally to a vehicle sanitizer system, and one or more methods of sanitizing a vehicle.

BACKGROUND

Sanitizing one or more surfaces of a cabin area of a vehicle may be conducted via a system comprising a lamp emitting ultraviolet (UV) light or infrared (IR) which kill bacteria/viruses. Although UV lights are used to sanitize surfaces within the vehicle, UV lights and/or the mechanism used to emit the UV lights do not always reach hard to reach spaces or sanitize deep stains. Passengers may enter a vehicle and notice that there are some areas of a vehicle that are not actually clean even though UV lights had been activated prior to entering.

A system using UV lamps or IR lamps for sanitizing seat surfaces of a public mass transportation vehicle has used a retractable device. Such a system, however, is of a generally large overall size and also is not incorporated and discretely stowed inside a compartment of the vehicle. Moreover, such systems are not controlled to be automatically deployed pursuant to a schedule, user input, or automatically activated upon detection of a particle, virus, pollutant, soil spill, etc.

BRIEF SUMMARY

In accordance with one or more embodiments, a vehicle sanitizer system, by plasma jets using water vapor content in the cabin or generated via the vehicle HVAC system, facilitates cleaning of the interior of a vehicle cabin more precisely than conventional UV lights, will be utilized. Using plasma is also a dry method that leaves no residue so it can be used on soft materials such as vehicle seats. Since plasma wands are more precise, plasma will be able to clean pores of vehicle seats and small cracks within the vehicle's interior that UV lights typically cannot.

In accordance with one or more embodiments, a vehicle sanitizer system, comprises one or more of: a sanitizer emitter member, selectively moveable between a stowed position in a compartment of a vehicle cabin and a deployed position out of the compartment; a sensor module to detect an interior of the vehicle cabin as sensor data; and a vehicle sanitizer module, comprising one or more processors to execute a set of instructions that cause the vehicle sanitizer module to: conduct, in response to the detection, an analysis of the sensor data; identify, in response to the analysis, one or more target interior surfaces in the vehicle cabin to be sanitized; and cause, via the sanitizer emitter member and in response to the identification, generation of one or more sanitizer streams directed at the identified one or more target interior surfaces using water vapor content in the vehicle cabin.

In accordance with one or more embodiments, computer program product for a vehicle, the computer program product including at least one computer readable medium comprising a set of instructions, which when executed by one or more processors, cause the one or more processors to: detect an interior of a vehicle cabin; conduct, in response to the detection, an analysis of the vehicle cabin; identify, in response to the analysis, one or more target interior surfaces in the vehicle cabin to be sanitized; and cause, in response to the identification, generation of one or more sanitizer streams directed at the identified one or more target interior surfaces using water vapor content into the vehicle cabin.

In accordance with one or more embodiments, method of sanitizing a vehicle, the method comprising one or more of: detecting an interior of a vehicle cabin; conducting, in response to the detection, an analysis of the vehicle cabin; identifying, in response to the analysis, one or more target interior surfaces in the vehicle cabin to be sanitized; and causing, in response to the identification, generation of one or more sanitizer streams directed at the identified one or more target interior surfaces using water vapor content into the vehicle cabin.

In accordance with one or more embodiments, the sensor data comprises image data, and the analysis comprises a visual analysis of the image data. The image data may be associated with a detection of a presence of persons in the cabin, particles, debris, contaminants, pollutants, etc. on the one or more surfaces. As such, additional air filtration systems may also be employed for such detection.

In accordance with one or more embodiments, the instructions, when executed by the one or more processors, cause the one or more processors to: determine, in response to the visual analysis, the occupancy status of the vehicle cabin, and cause the generation of water vapor content into the vehicle cabin, the one or more sanitizer streams being present only when the vehicle cabin is determined to be in an unoccupied state.

In accordance with one or more embodiments, the one or more sanitizer streams comprise plasma, the sensor data comprises humidity data in the vehicle cabin, and conducting the analysis comprises conducting an analysis of the humidity data by comparing the detected current humidity level to a predetermined threshold humidity level.

In accordance with one or more embodiments, the instructions, when executed by the one or more processors, cause the one or more processors to activate, in response to the comparison and when the detected current humidity level is less than the predetermined threshold humidity level, a vehicle HVAC system to introduce water vapor content into the vehicle cabin.

In accordance with one or more embodiments, the instructions, when executed by the one or more processors, cause the one or more processors to deploy, in response to the identification, a sanitizer emitter member configured to generate the one or more plasma streams.

In accordance with one or more embodiments, the instructions, when executed by the one or more processors, cause the one or more processors to selectively manipulate a base member and a one or more arm members in a manner that activates the sanitizer emitter member from the stowed position to deployed position.

In accordance with one or more embodiments, the instructions, when executed by the one or more processors, cause the one or more processors to selectively activate one or more lights for the purpose of illuminating light in the vehicle cabin. This can occur concurrently with one or more of the detection sequence and the deployment of the sanitizer emitter member.

BRIEF DESCRIPTION OF THE SEVERAL VIEWS OF THE DRAWINGS

The various advantages of the embodiments of the present invention will become apparent to one skilled in the art by reading the following specification and appended claims, and by referencing the following drawings, in which:

DETAILED DESCRIPTION

Figure 1:
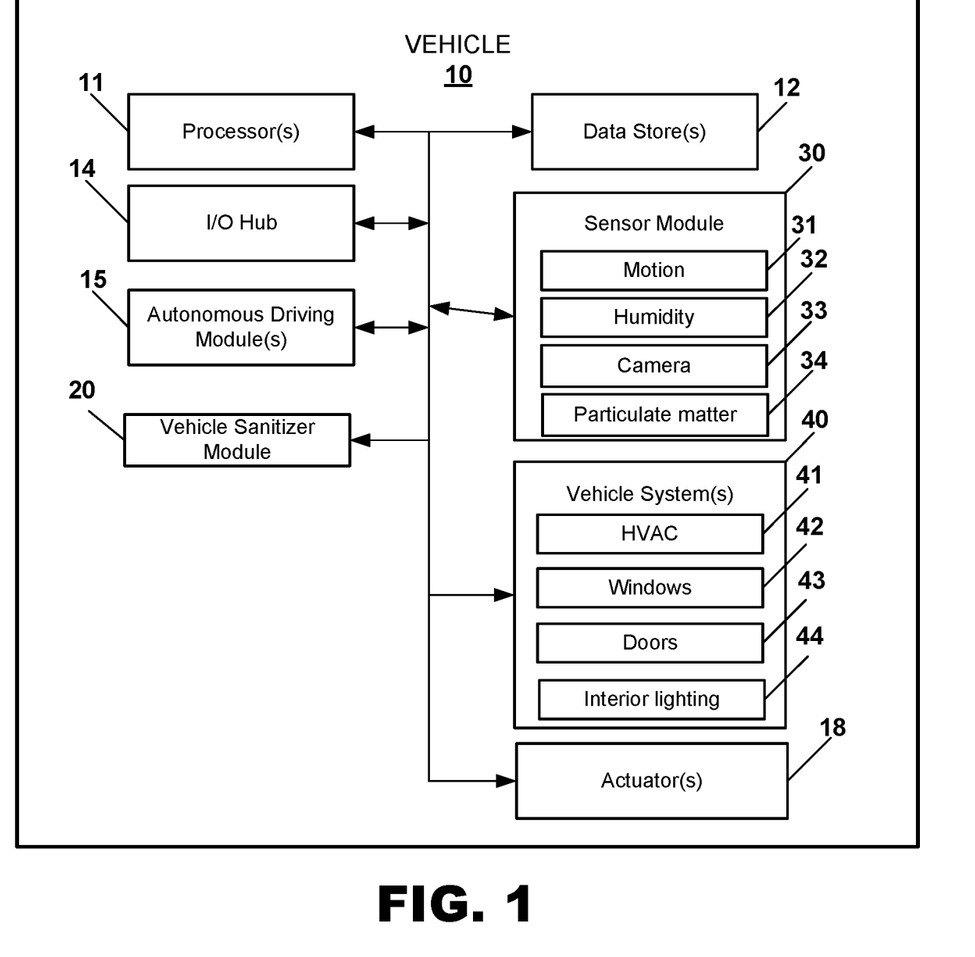
FIG. 1 illustrates an example vehicle, in accordance with one or more embodiments shown and described herein.

Turning to the figures, in which FIG. 1 illustrates a vehicle 10 that may comprise a mobility-as-a-service (MaaS) vehicle, a car, a truck, a van, a sport utility vehicle, a bus, etc. Embodiments, however, are not limited thereto, and thus, this disclosure contemplates the vehicle 10 comprising any suitable vehicle that falls within the spirit and scope of the principles of this disclosure. For example, the vehicle 10 may comprise a marine vehicle, an air vehicle, a space vehicle, or any other form of transport vehicle.

In accordance with one or more embodiments, the vehicle 10 may comprise an autonomous vehicle. As described herein, an "autonomous vehicle" may comprise a vehicle that is configured to operate in an autonomous mode. As set forth, described, and/or illustrated herein, "autonomous mode" means that one or more computing systems are used to operate, and/or navigate, and/or maneuver the vehicle along a travel route with minimal or no input from a human driver. In accordance with one or more embodiments, the vehicle 10 may be configured to be selectively switched between an autonomous mode and a manual mode. Such switching may be implemented in any suitable manner (now known or later developed). As set forth, described, and/or illustrated herein, "manual mode" means that operation, and/or navigation, and/or maneuvering of the vehicle along a travel route, may, either in whole or in part, is to be performed by a human driver.

In accordance with one or more embodiments, the vehicle 10 may comprise one or more operational elements, some of which may be a part of an autonomous driving system. Some of the possible operational elements of the vehicle 10 are shown in FIG. 1 and will now be described. It will be understood that it is not necessary for the vehicle 10 to have all the elements illustrated in FIG. 1 and/or described herein. The vehicle 10 may have any combination of the various elements illustrated in FIG. 1. Moreover, the vehicle 10 may have additional elements to those illustrated in FIG. 1.

In accordance with one or more embodiments, the vehicle 10 may not include one or more of the elements shown in FIG. 1. Moreover, while the various operational elements are illustrated as being located within the vehicle 10, embodiments are not limited thereto, and thus, one or more of the operational elements may be located external to the vehicle 10, and even physically separated by large spatial distances.

In accordance with one or more embodiments, the vehicle 10 comprises one or more processors 11. As set forth, described, and/or illustrated herein, "processor" means any component or group of components that are configured to execute any of the processes described herein or any form of instructions to carry out such processes or cause such processes to be performed. The processors 11 may be implemented with one or more general-purpose and/or one or more special-purpose processors. Examples of suitable processors include graphics processors, microprocessors, microcontrollers, DSP processors, and other circuitry that may execute software. Further examples of suitable processors include, but are not limited to, a central processing unit (CPU), an array processor, a vector processor, a digital signal processor (DSP), an opto-electronic processor, a field-programmable gate array (FPGA), a programmable logic array (PLA), an application specific integrated circuit (ASIC), programmable logic circuitry, and a controller. The processors 11 may comprise at least one hardware circuit (e.g., an integrated circuit) configured to carry out instructions contained in program code. In embodiments in which there is a plurality of processors 11, such processors 11 may work independently from each other, or one or more processors may work in combination with each other. In accordance with one or more embodiments, the processors 11 may be a host, main, or primary processor of the vehicle 10. For instance, the processors 11 may comprise an engine control unit (ECU). In accordance with one or more embodiments, the one or more processors 11 may also be deployed at the edge adjacent to the sanitizer apparatus.

In accordance with one or more embodiments, the vehicle 10 may comprise one or more autonomous driving modules 15. The autonomous driving modules 15 may be implemented as computer readable program code that, when executed by a processor, implement one or more of the various processes described herein, including, for example, determining a current driving maneuvers for the vehicle 10, future driving maneuvers and/or modifications. The autonomous driving modules 15 may also cause, directly or indirectly, such driving maneuvers or modifications thereto to be implemented. The autonomous driving modules 15 may be a component of one or more of the processors 11. Alternatively, the autonomous driving modules 15 may be executed on and/or distributed among other processing systems to which the processors 11 are operatively connected. The autonomous driving modules 15 may include instructions (e.g., program logic) executable by the processors 11. Such instructions may comprise instructions to execute various vehicle functions and/or to transmit data to, receive data from, interact with, and/or control the vehicle 10 or one or more systems thereof (e.g. one or more of vehicle systems 20). Alternatively or additionally, the data store(s) 12 may contain such instructions.

In accordance with one or more embodiments, the vehicle 10 may comprise an I/O hub 14 operatively connected to other systems of the vehicle 10. The I/O hub 14 may comprise an input interface and an output interface. The input interface and the output interface may be integrated as a single, unitary interface, or alternatively, be separate as independent interfaces that are operatively connected.

In one or more embodiments, the input interface may be used by a user, such as, for example, an operator of the vehicle to create one or more calendar events for automatic sanitization of the vehicle cabin. The input interface is defined herein as any device, component, system, element, or arrangement or groups thereof that enable information/data to be entered in a machine. The input interface may receive an input from a vehicle occupant (e.g. a driver or a passenger) or a remote operator of the vehicle 10. In an example, the input interface may comprise a user interface (UI), graphical user interface (GUI) such as, for example, a display, human-machine interface (HMI), or the like. Embodiments, however, are not limited thereto, and thus, the input interface may comprise a keypad, touch screen, multi-touch screen, button, joystick, mouse, trackball, microphone and/or combinations thereof.

The output interface is defined herein as any device, component, system, element or arrangement or groups thereof that enable information/data to be presented to a vehicle occupant and/or remote operator of the vehicle 10. The output interface may be configured to present information/data to the vehicle occupant and/or the remote operator. The output interface may comprise one or more of a visual display or an audio display such as a microphone, earphone, and/or speaker. One or more components of the vehicle 10 may serve as both a component of the input interface and a component of the output interface.

In accordance with one or more embodiments, the vehicle 10 may comprise one or more data stores 12 to for storing one or more types of data. The vehicle 10 may include interfaces that enable one or more systems thereof to manage, retrieve, modify, add, or delete, the data stored in the data stores 12. The data stores 12 may comprise volatile and/or non-volatile memory. Examples of suitable data stores 12 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data stores 12 may be a component of the processors 11, or alternatively, may be operatively connected to the processors 11 for use thereby. As set forth, described, and/or illustrated herein, "operatively connected" may include direct or indirect connections, including connections without direct physical contact.

In accordance with one or more embodiments, the vehicle 10 may comprise a sensor module 30 configured to, at least during operation of the vehicle 10, dynamically detect, determine, assess, monitor, measure, quantify, and/or sense information about the vehicle 10, including the vehicle cabin and the driving environment external to the vehicle 10. As set forth, described, and/or illustrated herein, "sensor" means any device, component and/or system that can perform one or more of detecting, determining, assessing, monitoring, measuring, quantifying, and sensing something. The one or more sensors may be configured to detect, determine, assess, monitor, measure, quantify and/or sense in real-time. As set forth, described, and/or illustrated herein, "real-time" means a level of processing responsiveness that a user or system senses as sufficiently immediate for a particular process or determination to be made, or that enables the processor to keep up with some external process.

Alternatively or additionally, the sensor module 30 may comprise one or more sensors, including motion sensors 31, humidity sensors 32, image sensors or cameras 33, and particulate matter sensors 34. The one or more sensors 31-34 may be configured to detect, determine, assess, monitor, measure, quantify, and/or sense information about the vehicle cabin and the external environment in which the vehicle 10 is located, including information about other vehicles in the external environment. Various examples of these and other types of sensors will be described herein. It will be understood that the embodiments are not limited to the particular sensors described herein.

The sensor module 30 and/or the one or more sensors 31-34 may be operatively connected to the processors 11, the data stores 12, the autonomous driving module 15 and/or other elements, components, modules of the vehicle 10. The sensor module 30 and/or any of the one or more sensors 31-34 described herein may be provided or otherwise positioned in any suitable location with respect to the vehicle 10. For example, one or more sensors 31-34 may be located within one or more of the cabin of the vehicle 10 and a component of the vehicle 10. This disclosure contemplates the one or more sensors 31-34 may be positioned in any suitable location that permits practice of the one or more embodiments.

In accordance with one or more embodiments, the one or more sensors 31-34 may work independently from each other, or alternatively, may work in combination with each other. The sensors 31-34 may be used in any combination, and may be used redundantly to validate and improve the accuracy of the detection.

In accordance with one or more embodiments, the sensor module 30 may comprise one or more image devices such as, for example, one or more cameras 33. As set forth, described, and/or illustrated herein, "camera" means any device, component, and/or system that can capture visual data. Such visual data may include one or more of video information/data and image information/data. The visual data may be in any suitable form. The one or more cameras 33 may comprise high resolution cameras. The high resolution can refer to the pixel resolution, the spatial resolution, spectral resolution, temporal resolution, and/or radiometric resolution. In accordance with one or more embodiments, the one or more cameras 33 may comprise high dynamic range (HDR) cameras or infrared (IR) cameras.

In accordance with one or more embodiments, one or more of the cameras 33 may comprise a lens and an image capture element. The image capture element may be any suitable type of image capturing device or system, including, for example, an area array sensor, a charge coupled device (CCD) sensor, a complementary metal oxide semiconductor (CMOS) sensor, a linear array sensor, and/or a CCD (monochrome). The image capture element may capture images in any suitable wavelength on the electromagnetic spectrum. The image capture element may capture color images and/or grayscale images. One or more of the cameras may be configured with zoom in and/or zoom out capabilities.

In accordance with one or more embodiments, one or more of the cameras 33 may be spatially oriented, positioned, configured, operable, and/or arranged to capture visual data from the interior cabin of the vehicle 10. The one or more of cameras 33 may be fixed in a position that does not change relative to the vehicle cabin. Alternatively or additionally, one or more of the cameras 33 may be movable so as to change position relative to the vehicle cabin in a manner which facilitates the capture of visual data from different portions of the vehicle cabin. Such movement of one or more of the cameras 33 may be achieved in any suitable manner, such as, for example, by rotation (about one or more rotational axes), by pivoting (about a pivot axis), by sliding (along an axis), and/or by extending (along an axis). The one or more cameras 33 (and/or the movement thereof) may be controlled by one or more of the processors 11, the sensor module 30, and any one or more of the modules set forth, described, and/or illustrated herein.

In accordance with one or more embodiments, the vehicle 10 may comprise a vehicle sanitizer module 20. Operation of the vehicle sanitizer module 20 may be implemented as computer readable program code that, when executed by a processor, implement one or more of the various processes set forth, described, and/or illustrated herein, including, for example, to detect one or more vehicles in the driving environment. The vehicle sanitizer module 20 may be a component of the processors 11, or alternatively, may be executed on and/or distributed among other processing systems to which the processors 11 are operatively connected. The vehicle sanitizer module 20 may include a set of logic instructions executable by the processors 11. Alternatively or additionally, the data stores 12 may contain such logic instructions. The logic instructions may include assembler instructions, instruction set architecture (ISA) instructions, machine instructions, machine dependent instructions, microcode, state-setting data, configuration data for integrated circuitry, state information that personalizes electronic circuitry and/or other structural components that are native to hardware (e.g., host processor, central processing unit/CPU, microcontroller, etc.).

The vehicle sanitizer module 20 may be configured to facilitate sanitization of the vehicle cabin, as will be described in greater detail hereinafter. For example, the sensor module 30 may generate sensor data associated with the vehicle cabin, and the one or more processors 11 may be configured to conduct an analysis of the sensor data, identify one or more target interior surfaces TS in the vehicle cabin to be sanitized based on the analyzed data, and then facilitate sanitizing of the target interior surfaces TS. The captured sensor data may be located in a vehicle image database of the data stores 12 or an external source (e.g., cloud-based data store(s)).

In accordance with one or more embodiments, one or more of the modules 15, 20 set forth, described, and/or illustrated herein may include artificial or computational intelligence elements, e.g., neural network, fuzzy logic, or other machine learning algorithms.

In accordance with one or more embodiment, the vehicle 10 may comprise one or more vehicle systems 40, including but not limited to an HVAC system 41, a windows system 42, a door system 43, interior lighting system 44, etc. Embodiments, however, are not limited thereto, and thus, this disclosure contemplates the vehicle 10 comprising more, fewer, or different systems or subsystems. In the illustrated example of FIG. 4, one or more of the vehicle systems 40 may form a subsystem comprising, for example, one or more of a base 21, arm members 23, sanitizer or plasma emitter member 24, windows 42, doors 43, interior lighting 44 which are controlled by the vehicle sanitizer module 40 or the one or more processors 11.

Figure 4:
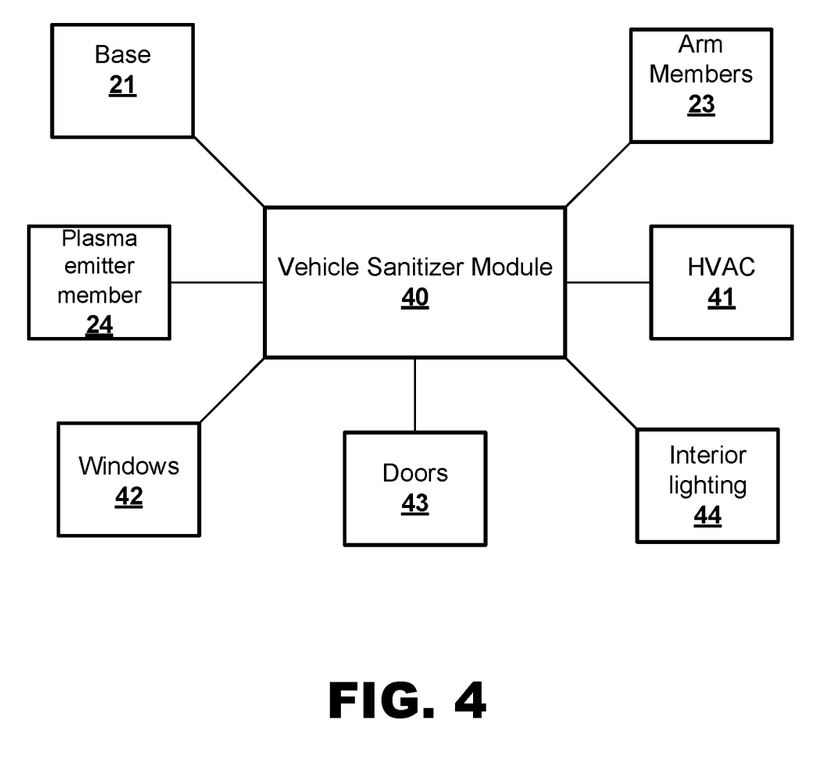
FIG. 4 illustrates an example vehicle subsystem that includes the vehicle sanitizer module, in accordance with one or more embodiments shown and described herein.

In accordance with one or more embodiment, one or more of the processors 11, the autonomous driving module 15, and the vehicle sanitizer module 20 may be operatively connected to communicate with the various vehicle systems 40 and/or individual components thereof. For example, one or more of the processors 11 and the vehicle sanitizer module 20 may be in communication to send and/or receive information from the various vehicle systems 40 to control the movement, speed, maneuvering, heading, direction, etc. of the vehicle 10. One or more of the processors 11 and the vehicle sanitizer module 20 may control some or all of the vehicle systems 40, and thus, may be partially or fully autonomous.

The vehicle 10 may comprise one or more actuators 18, which may be any element or combination of elements configured to modify, adjust and/or alter one or more of the vehicle systems 40 or components thereof in response to receiving signals or other inputs from one or more of the processors 11, the autonomous driving module 15, and the vehicle sanitizer module 20. Any suitable actuator may be used. For instance, the one or more actuators 18 may comprise motors, pneumatic actuators, hydraulic pistons, relays, solenoids, and/or piezoelectric actuators, etc.

The vehicle sanitizer module 20 is operatively connected to a vehicle sanitizer apparatus comprising, for example, the plasma emitter member 24 that is selectively moveable between a stowed position (FIG. 2) in a compartment C (e.g., a vehicle roof) of the vehicle 10 and a deployed position (FIG. 3) from the compartment C to generate and emit one or more pressurized non-thermal plasma streams (PS) to sanitize one or more target interior surfaces (TS) in the vehicle cabin. This disclosure contemplates the interior surfaces TS in the cabin to be the vehicle doors, vehicle trim, vehicle seats, vehicle floor, vehicle arm rests, vehicle dashboard, vehicle instrument panel, vehicle displays, vehicle mirrors, and any other exposed location or high touch surface in the vehicle cabin.

Figure 2:
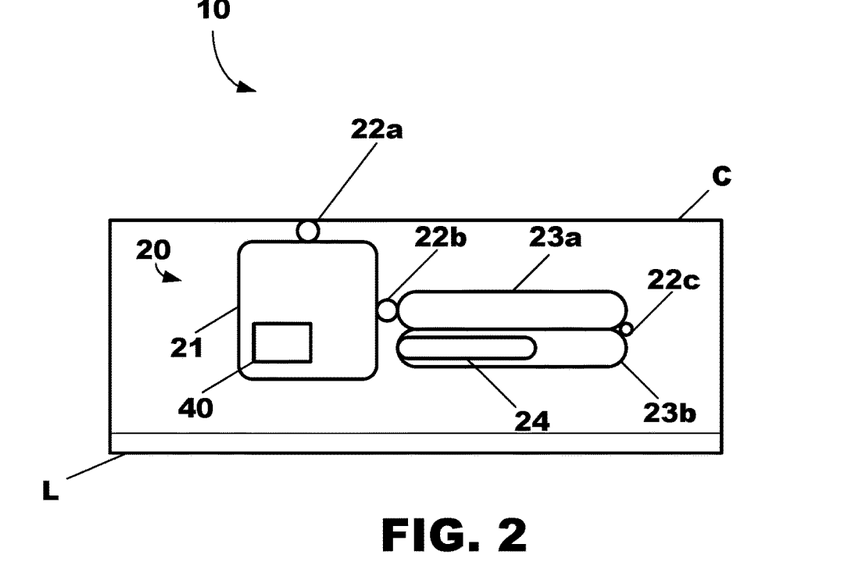
FIG. 2 illustrates an example vehicle sanitizer apparatus, in a stowed position, in accordance with one or more embodiments shown and described herein.
Figure 3:
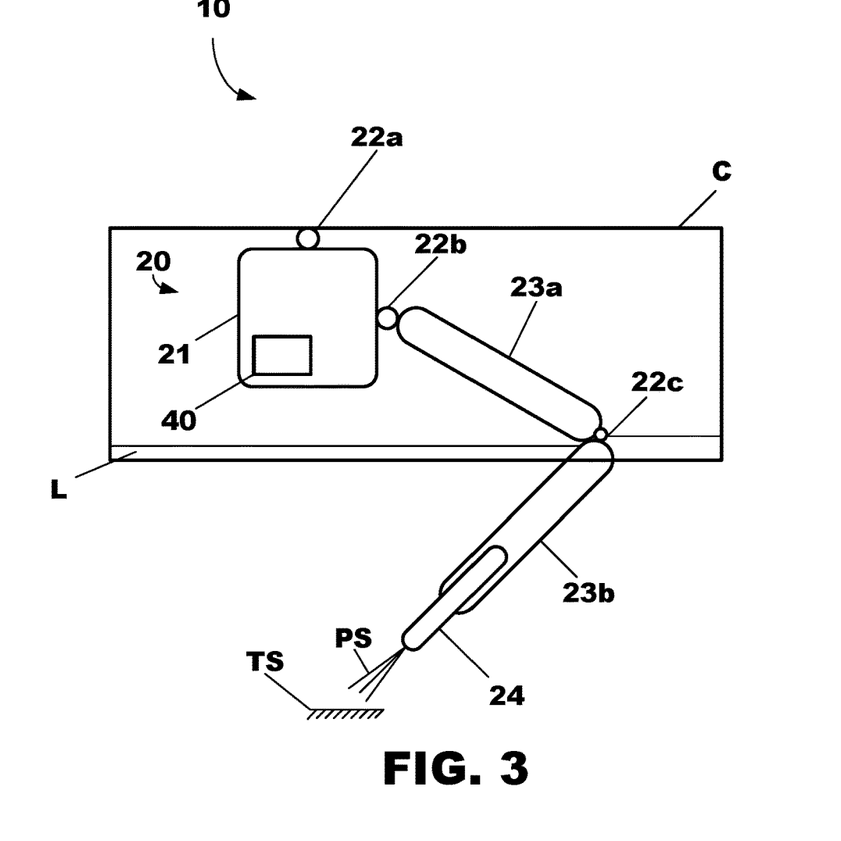
FIG. 3 illustrates an example of the vehicle sanitizer apparatus of FIG. 1, in a deployed position.

While the illustrated example contemplates implementing an emitter member 24 that is configured to generate and emit plasma, embodiments are not limited thereto. This disclosure contemplates an emitter member that emits any suitable sanitizing agent that falls within the spirit and scope of the principles of this disclosure.

Also, while the illustrated example contemplates the stowing of the vehicle sanitizer apparatus and the components thereof in a compartment C of the vehicle roof, embodiments are not limited thereto. This disclosure contemplates stowing the vehicle sanitizer apparatus and the components thereof in any suitable vehicle compartment that falls within the spirit and scope of the principles of this disclosure. For example, the compartment C may be located in one or more of the vehicle doors, vehicle floor, vehicle arm rests, vehicle dashboard, vehicle instrument panel, vehicle center console, and any other location in the vehicle cabin.

The plasma emitter member 24 is to generate and emit one or more plasma streams PS or plasma plumes produced from air and water vapor content. The water vapor content can be moisture from ambient air within the vehicle cabin itself or moisture generated via the vehicle HVAC system. During a sanitization sequence, one or more plasma fields is generated by the plasma emitter member 24. Water molecules from water vapor content in the ambient air of the vehicle cabin enters the plasma field(s). The plasma field breaks down the water vapor content in a manner that hydroxyl radicals attack organic molecules, decomposing them into carbon dioxide and water.

In one or more examples, plasma emitter member 24 comprises a wand having a main body and a head having one or more nozzles or dispensers to direct the one or more plasma plumes PS towards a target surface TS. The head may have a structural configuration to facilitate precise sanitizing of the target surface TS while also having the capability of accessing hard-to-reach areas in the vehicle cabin. In one or more embodiments, the plasma emitter member 24 is composed of a polymer or composite material. Embodiments, however, are not limited thereto, and thus, this disclosure contemplates plasma emitter member 24 being composed of any suitable material that falls within the spirit and scope of the principles of this disclosure set forth herein.

The plasma emitter member 24 is connected to a pivotably moveable robotic arm comprising one or more linkages or arm members 23a, 23b. The arm members 23a, 23b are configured for articulating or pivotal movement via actuators with ball joint members 22b, 22c to selectively move the plasma emitter member 24 between the stowed position and the deployed position in response to a control signal from a vehicle sanitizer module 20. The connection between the plasma emitter member 24 and the arm members 23a, 23b facilitates orientation of the plasma emitter member 24 at an angle suitable for sanitizing a target surface TS via plasma streams PS.

In one or more embodiments, the plasma emitter member 24 may be telescopically connected to the arm members 23a, 23b for selective movement using integrated actuators in a direction along a longitudinal axis of the plasma emitter member 24 between a partially or fully retracted position inside an arm member 23b and a partially or fully extended position when performing one or more tasks (i.e., sensing, illuminating, detecting, increasing water vapor content, etc.) during a sanitizing sequence. Embodiments, however, are not limited thereto. This disclosure contemplates a connection between the arm members 23a, 23b and the plasma emitter member 24 in any suitable manner falls within the spirit and scope of the principles of this disclosure.

The multi-jointed arm comprises one or more arm members 23a, 23b that are connected to a base member 21 via a ball joint and actuator member 22b. The base member 21 is rotatably connected to the compartment C at a fixed point defined by the ball joint member 22a. Through this connection, the base member 21 is configured to rotate via an actuator between approximately 0 to 360 degrees about a fixed axis relative to the compartment C in response to a control signal from the vehicle sanitizer module 20. In that way, the base member 21 selectively facilitates access by the vehicle sanitizer apparatus to hard-to-reach areas of the vehicle cabin. In one or more embodiments, the arm members 23a, 23b is composed of a metal, metal alloy, or lightweight composite material. Embodiments, however, are not limited thereto, and thus, this disclosure contemplates the arm members 23a, 23b being composed of any suitable material that falls within the spirit and scope of the principles of this disclosure set forth herein.

In one or more embodiments, the compartment C defines a space sized to receive the base member 21, the arm members 23a, 23b, and the plasma emitter member 24 in the stowed position of the plasma emitter member 24. The space may be closed by a lid L that is automatically or selectively moveable (i.e., pivotally and/or linearly) between a closed position in a stowed position of the plasma emitter member 24, and an open position in a deployed position of the plasma emitter member 24.

Figure 5:
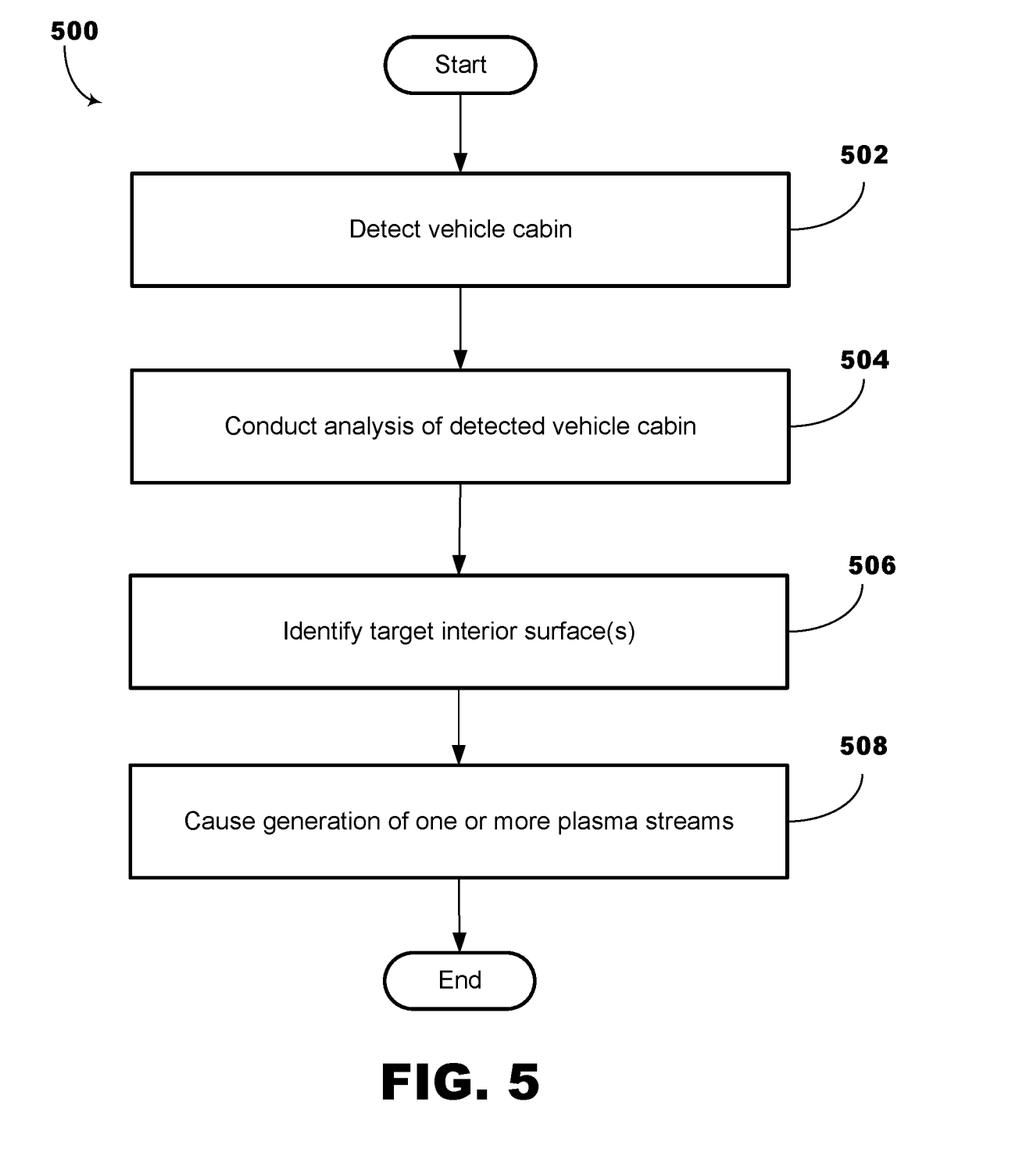
FIGS. 5 and 6 illustrate a schematic diagram of example methods of sanitizing a vehicle, in accordance with one or more embodiments shown and described herein.
Figure 6:
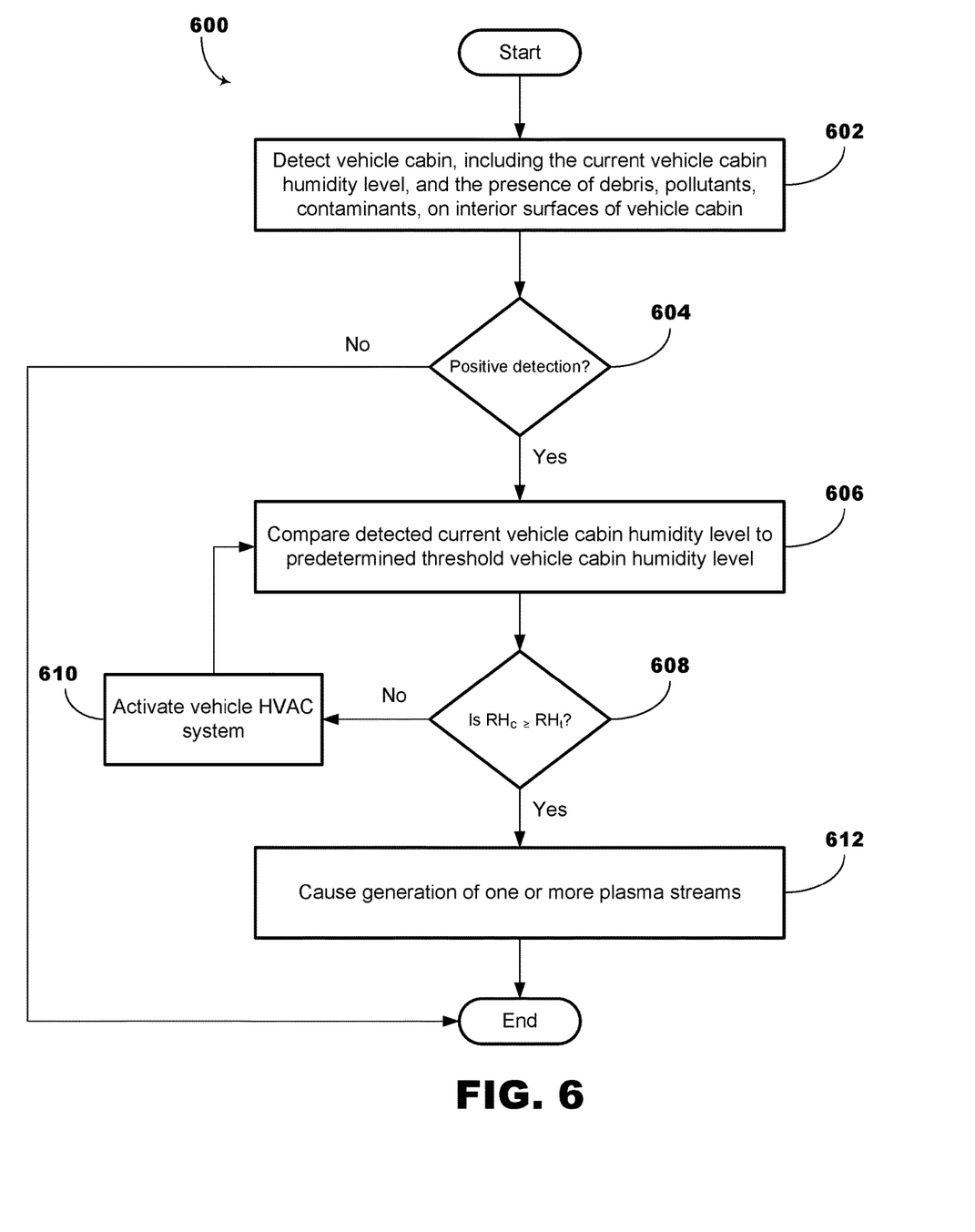

In the illustrated examples of FIGS. 5 and 6, a flowchart of methods 500 and 600 of sanitizing a vehicle is shown. In one or more examples, the respective flowcharts of the methods 500 and 600 may be implemented by the one or more processors 11. For example, the one or more processors 11 are configured to implement the methods 500 and 600 using logic instructions (e.g., software), configurable logic, fixed-functionality hardware logic, etc., or any combination thereof. In one or more examples, software executed by the vehicle sanitizer module 20 or the control module 50 provides functionality described or illustrated herein. In particular, software executing by the one or more processors 11 is configured to perform one or more processing blocks of the methods 500 and 600 set forth, described, and/or illustrated herein, or provides functionality set forth, described, and/or illustrated.

In the illustrated example of FIG. 5, illustrated process block 502 includes detecting the vehicle cabin. The detection is conducted to acquire image data in the vehicle cabin, humidity data in the vehicle cabin, particulate matter data in the vehicle cabin, etc.

The method 500 may then proceed to illustrated process block 504, which includes conducting, in response to the detection, an analysis of the vehicle cabin. Conducting the analysis comprises conducting a visual analysis of the image data or particulate matter analysis of the air.

The method 500 may then proceed to illustrated process block 506, which includes identifying, in response to the analysis, one or more target interior surfaces in the vehicle cabin to be sanitized.

The method 500 may then proceed to illustrated process block 508, which includes deploying a sanitizer emitter member, in response to the identification, and causing generation one or more plasma streams that are to be directed at the identified one or more target interior surfaces. The method 500 may terminate or end after execution of process block 508.

In the illustrated example of FIG. 6, illustrated process block 602 includes detecting a presence of debris, pollutants, contaminants on one or more surfaces of the vehicle cabin.

The method 600 may then proceed to illustrated process block 604, which includes a determination of whether a positive detection has occurred. If "No," the method 600 may terminate or end.

If "Yes," the method 600 may then proceed to illustrated process block 606, which includes comparing the detected current humidity level to a predetermined threshold humidity level.

The method 600 may then proceed to illustrated process block 608, which includes a determination of whether the detected current humidity level RHc is greater than or equal to a predetermined threshold humidity level RHt.

If "No," the method 600 proceeds to illustrated process block 610, which includes activating a vehicle HVAC system to introduce water vapor content into the vehicle cabin. The method 600 may then return to illustrated process block 606.

If "Yes," the method 600 proceeds to illustrated process block 612, which includes deploying a sanitizer emitter member, in response to the identification, and causing generation one or more plasma streams directed at the identified one or more target interior surfaces. The method 500 may terminate or end after execution of process block 508.

The terms "coupled," "attached," or "connected" may be used herein to refer to any type of relationship, direct or indirect, between the components in question, and may apply to electrical, mechanical, fluid, optical, electromagnetic, electromechanical or other connections. Additionally, the terms "first," "second," etc. are used herein only to facilitate discussion, and carry no particular temporal or chronological significance unless otherwise indicated. The terms "cause" or "causing" means to make, force, compel, direct, command, instruct, and/or enable an event or action to occur or at least be in a state where such event or action may occur, either in a direct or indirect manner.

Those skilled in the art will appreciate from the foregoing description that the broad techniques of the embodiments of the present invention may be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. A vehicle sanitizer system, comprising:
a sanitizer emitter member, selectively moveable between a stowed position in a compartment of a vehicle cabin and a deployed position out of the compartment;
a sensor module to detect an interior of the vehicle cabin as sensor data; and a vehicle sanitizer module, comprising one or more processors to execute a set of instructions that cause the vehicle sanitizer module to:
- conduct, in response to the detection, an analysis of the sensor data;
- identify, in response to the analysis, one or more target interior surfaces in the vehicle cabin to be sanitized;
- cause, in response to the identification, generation of one or more sanitizer streams using water vapor content in the vehicle cabin; and
- cause, via the sanitizer emitter member, sanitizing of the identified one or more target interior surfaces by directing the one or more sanitizer streams produced from the water vapor content at the identified one or more target interior surfaces.

2. The vehicle sanitizer system of claim 1, wherein:
the one or more sanitizer streams comprise plasma,
the sensor data comprises image data, and
the analysis comprises a visual analysis of the image data.

3. The vehicle sanitizer system of claim 2, wherein the instructions, when executed by the one or more processors, cause the one or more processors to:
- determine, in response to the visual analysis, an occupancy status of the vehicle cabin, and
- cause the generation of the one or more sanitizer streams only when the vehicle cabin is determined to be in an unoccupied state.

4. The vehicle sanitizer system of claim 1, wherein:
the sensor data comprises humidity data in the vehicle cabin, and
conducting the analysis comprises conducting an analysis of the humidity data by comparing the detected current humidity level to a predetermined threshold humidity level.

5. The vehicle sanitizer system of claim 4, wherein the instructions, when executed by the one or more processors, cause the one or more processors to activate, in response to the comparison and when the detected current humidity level is less than the predetermined threshold humidity level, a vehicle HVAC system to introduce water vapor content into the vehicle cabin.

6. The vehicle sanitizer system of claim 1, wherein the instructions, when executed by the one or more processors, cause the one or more processors to deploy, in response to the identification, a sanitizer emitter member configured to generate the one or more sanitizer streams.

7. The vehicle sanitizer system of claim 6, wherein the instructions, when executed by the one or more processors, cause the one or more processors to selectively manipulate a base member and a one or more arm members via actuators in a manner that activates the sanitizer emitter member from the stowed position to the deployed position.

8. A computer program product for a vehicle, the computer program product including at least one computer readable medium comprising a set of instructions, which when executed by one or more processors, cause the one or more processors to:
- detect an interior of a vehicle cabin;
- conduct, in response to the detection, an analysis of the vehicle cabin;
- identify, in response to the analysis, one or more target interior surfaces in the vehicle cabin to be sanitized; and
- cause, in response to the identification, generation of one or more sanitizer streams using water vapor content in the vehicle cabin; and
- cause, via the sanitizer emitter member, sanitizing of the identified one or more target interior surfaces by directing the one or more sanitizer streams produced from the water vapor content at the identified one or more target interior surfaces.

9. The computer program product of claim 8, wherein:
the one or more sanitizer streams comprise plasma,
the sensor data comprises image data, and
conducting the analysis comprises conducting a visual analysis of the image data.

10. The computer program product of claim 9, wherein the instructions, when executed by the one or more processors, cause the one or more processors to:
- determine, in response to the visual analysis, an occupancy status of the vehicle cabin, and
- cause the generation of the one or more sanitizer streams only when the vehicle cabin is determined to be in an unoccupied state.

11. The computer program product of claim 10, wherein:
the sensor data comprises humidity data in the vehicle cabin, and
conducting the analysis comprises conducting an analysis of the humidity data by comparing the detected current humidity level to a predetermined threshold humidity level.

12. The computer program product of claim 11, wherein the instructions, when executed by the one or more processors, cause the one or more processors to activate, in response to the comparison and when the detected current humidity level is less than the predetermined threshold humidity level, a vehicle HVAC system to introduce water vapor content into the vehicle cabin.

13. The computer program product of claim 8, wherein the instructions, when executed by the one or more processors, cause the one or more processors to deploy, in response to the identification, a sanitizer emitter member configured to generate the one or more sanitizer streams.

14. The computer program product of claim 8, wherein the instructions, when executed by the one or more processors, cause the one or more processors to selectively manipulate a base member and a one or more arm members in a manner that deploys the sanitizer emitter member.

15. A method of sanitizing a vehicle, the method comprising:
- detecting an interior of the vehicle cabin;
- conducting, in response to the detection, an analysis of the vehicle cabin;
- identifying, in response to the analysis, one or more target interior surfaces in the vehicle cabin to be sanitized; and
- causing, in response to the identification, generation of one or more sanitizer streams using water vapor content in the vehicle cabin; and
- cause, via the sanitizer emitter member, sanitizing of the identified one or more target interior surfaces by directing the one or more sanitizer streams produced from the water vapor content at the identified one or more target interior surfaces.

16. The method of claim 15, wherein:
the detection is conducted to acquire image data in the vehicle cabin, and
conducting the analysis comprises conducting a visual analysis of the image data.

17. The method of claim 15, further comprising:
determining, in response to the visual analysis, the occupancy status of the vehicle cabin, and causing the generation of the one or more sanitizer streams only when the vehicle cabin is determined to be in an unoccupied state.

18. The method of claim 15, wherein:

the detection is conducted to acquire humidity data in the vehicle cabin, and conducting the analysis comprises conducting an analysis of the humidity data by comparing the detected current humidity level to a predetermined threshold humidity level.

19. The method of claim 18, further comprising activating, in response to the comparison and when the detected current humidity level is less than the predetermined threshold humidity level, a vehicle HVAC system to introduce water vapor content into the vehicle cabin.

20. The method of claim 15, further comprising deploying, in response to the identification, a sanitizer emitter member configured to generate the one or more sanitizer streams.

* * * * *